(12) United States Patent
Holmes et al.

(10) Patent No.: US 6,412,117 B1
(45) Date of Patent: Jul. 2, 2002

(54) DECORATIVE TRACH TIE COVER

(76) Inventors: Bridgett Holmes; Erma Randle, both of 1715 Sunflower Ave. #7, Glendora; Jayne Hallahan, deceased, late of Glendora; by Kay H. Crowder, legal representative, 1715 Sunflower Ave. #7, Glenora, all of CA (US) 91740

( * ) Notice: Subject to any disclaimer, the term of this patent is extended or adjusted under 35 U.S.C. 154(b) by 0 days.

(21) Appl. No.: 09/901,769

(22) Filed: Jul. 10, 2001

(51) Int. Cl.[7] .......................... A41D 23/00; A61M 25/02
(52) U.S. Cl. ...................................... 2/137; 128/207.17
(58) Field of Search .............................. 2/137, 1, 181.2, 2/170, 91, 916, DIG. 11, 468, 59; D2/600; 128/DIG. 15, 207.17

(56) References Cited

U.S. PATENT DOCUMENTS

| | | | | |
|---|---|---|---|---|
| 2,806,471 A | * | 9/1957 | Breese | |
| 2,998,695 A | * | 9/1961 | Cornett | |
| 4,266,511 A | * | 5/1981 | Muench | 119/106 |
| 4,313,437 A | * | 2/1982 | Martin | 128/207.17 |
| 4,331,144 A | * | 5/1982 | Wapner | 128/207.17 |
| 4,654,897 A | * | 4/1987 | Rosaen | 2/207 |
| 5,101,822 A | * | 4/1992 | Kimmel | 128/207.14 |
| 5,133,084 A | * | 7/1992 | Martin | 2/2 |
| 5,305,470 A | * | 4/1994 | McKay | 2/7 |
| 5,357,952 A | * | 10/1994 | Schuster et al. | 128/207.17 |
| 5,456,274 A | * | 10/1995 | Selbee et al. | 132/275 |
| 5,546,938 A | * | 8/1996 | McKenzie | 128/207.17 |
| 5,619,778 A | * | 4/1997 | Sloot | 24/715.4 |
| 6,023,786 A | * | 2/2000 | Burnett | 2/170 |
| 6,058,517 A | * | 5/2000 | Hartunian | 2/468 |

* cited by examiner

*Primary Examiner*—Gloria M. Hale
*Assistant Examiner*—Alissa L. Hoey
(74) *Attorney, Agent, or Firm*—Goldstein & Lavas, P.C.

(57) ABSTRACT

A decorative trach tie cover including a flexible tube having opposed open ends. The flexible tube receives the collar tie of the trachea tube therein. The flexible tube has a length about equal to a length of the collar tie of the trachea tube. The flexible tube is constructed of a soft and comfortable fabric.

3 Claims, 2 Drawing Sheets

DECORATIVE TRACH TIE COVER

BACKGROUND OF THE INVENTION

The present invention relates to a decorative trach tie cover and more particularly pertains to covering the collar tie of a trachea tube to coordinate with selected items of clothing.

The use of holding and coupling devices is known in the prior art. More specifically, holding and coupling devices heretofore devised and utilized for the purpose of holding and containing various objects are known to consist basically of familiar, expected and obvious structural configurations, notwithstanding the myriad of designs encompassed by the crowded prior art which have been developed for the fulfillment of countless objectives and requirements.

By way of example, U.S. Pat. No. 6,047,699 to Ryatt discloses a ventilator and trach holder assembly. U.S. Pat. No. 5,619,778 to Sloot and U.S. Pat. No. 6,052,921 to Oreck disclose various shoe lace devices.

While these devices fulfill their respective, particular objective and requirements, the aforementioned patents do not describe a decorative trach tie cover for covering the collar tie of a trachea tube to coordinate with selected items of clothing.

In this respect, the decorative trach tie cover according to the present invention substantially departs from the conventional concepts and designs of the prior art, and in doing so provides an apparatus primarily developed for the purpose of covering the collar tie of a trachea tube to coordinate with selected items of clothing.

Therefore, it can be appreciated that there exists a continuing need for a new and improved decorative trach tie cover which can be used for covering the collar tie of a trachea tube to coordinate with selected items of clothing. In this regard, the present invention substantially fulfills this need.

SUMMARY OF THE INVENTION

In the view of the foregoing disadvantages inherent in the known types of holding and coupling devices now present in the prior art, the present invention provides an improved decorative trach tie cover. As such, the general purpose of the present invention, which will be described subsequently in greater detail, is to provide a new and improved decorative trach tie cover which has all the advantages of the prior art and none of the disadvantages.

To attain this, the present invention essentially comprises a flexible tube having opposed open ends. The flexible tube receives the collar tie of the trachea tube therein. The flexible tube has a length about equal to a length of the collar tie of the trachea tube. The flexible tube is constructed of a soft and comfortable fabric.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved decorative trach tie cover which has all the advantages of the prior art holding and coupling devices and none of the disadvantages.

It is another object of the present invention to provide a new and improved decorative trach tie cover which may be easily and efficiently manufactured and marketed.

It is a further object of the present invention to provide a new and improved decorative trach tie cover which is of durable and reliable construction.

An even further object of the present invention is to provide a new and improved decorative trach tie cover which is susceptible of a low cost of manufacture with regard to both materials and labor, and which accordingly is then susceptible of low prices of sale to the consuming public, thereby making such a decorative trach tie cover economically available to the buying public.

Even still another object of the present invention is to provide a new and improved decorative trach tie cover for covering the collar tie of a trachea tube to coordinate with selected items of clothing.

Lastly, it is an object of the present invention to provide a new and improved decorative trach tie cover including a flexible tube having opposed open ends. The flexible tube receives the collar tie of the trachea tube therein. The flexible tube has a length about equal to a length of the collar tie of the trachea tube. The flexible tube is constructed of a soft and comfortable fabric.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various figures.

DESCRIPTION OF THE PREFERRED EMBODIMENT

Figure 1:
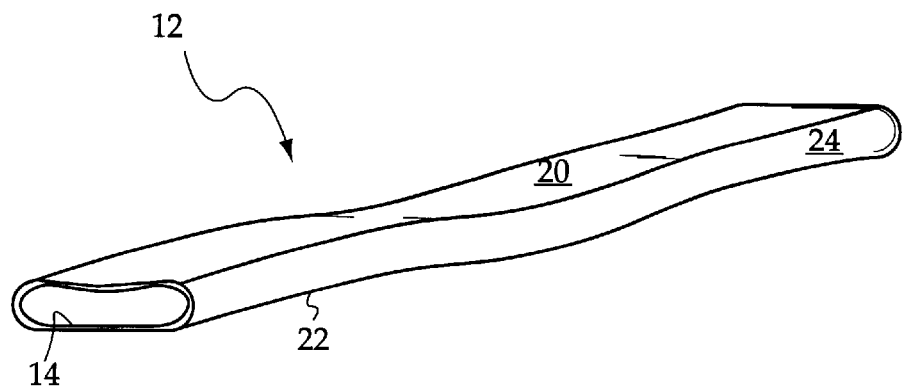
FIG. 1 is a perspective view of the preferred embodiment of the decorative trach tie cover constructed in accordance with the principles of the present invention.
Figure 2:
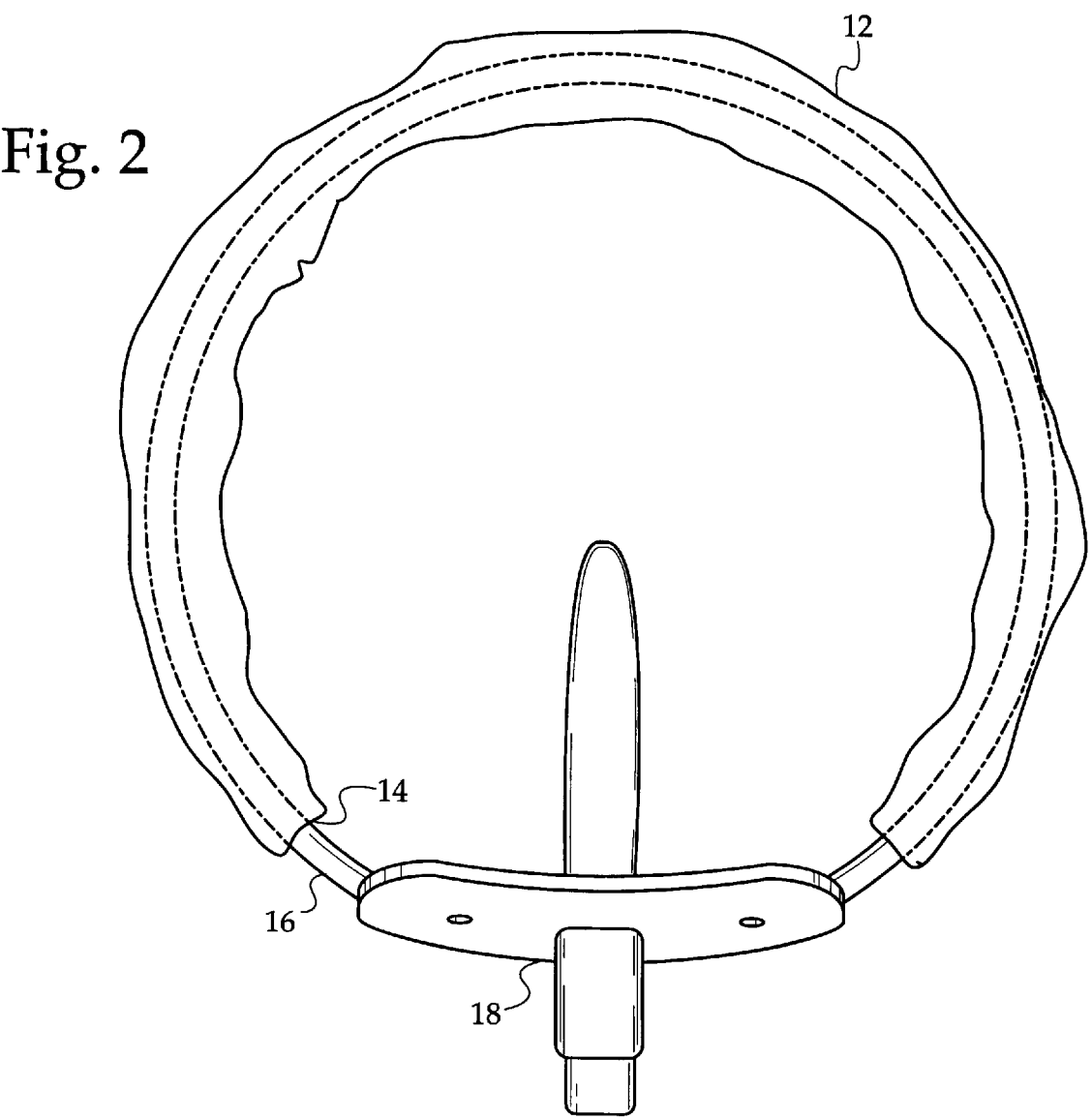
FIG. 2 is a top plan view of the present invention illustrated in place on the collar tie for a trachea tube.
Figure 3:
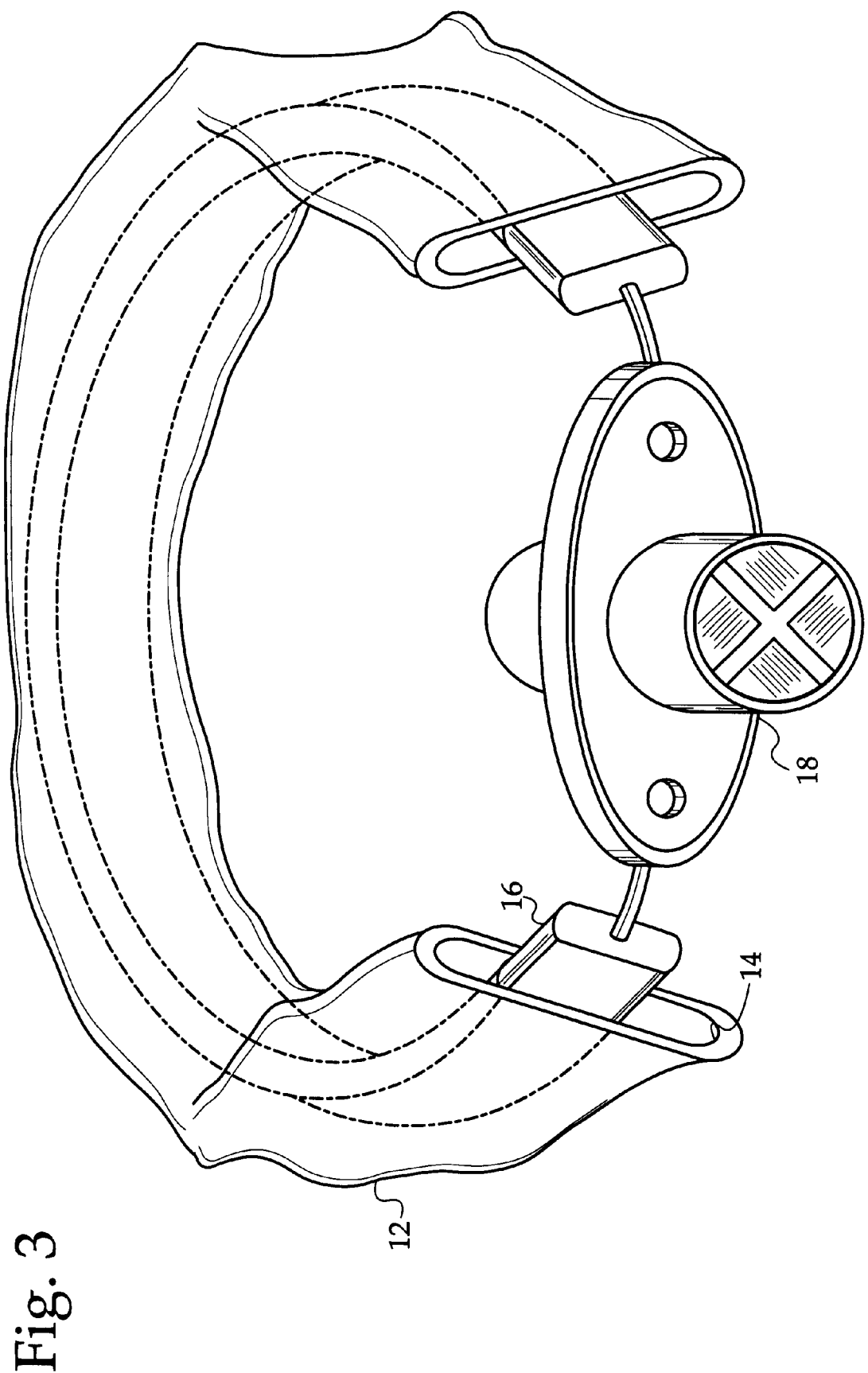
FIG. 3 is a perspective view of the present invention illustrated in place on the collar tie for a trachea tube.

With reference now to the drawings, and in particular, to FIGS. 1 through 3 thereof, the preferred embodiment of the new and improved decorative trach tie cover embodying the principles and concepts of the present invention and generally designated by the reference number 12 will be described.

Specifically, it will be noted in the various Figures that the device relates to a decorative trach tie cover for covering the collar tie of a trachea tube to coordinate with selected items of clothing.

The present invention is essentially comprised of a flexible tube 12. The flexible tube 12 has opposed open ends 14. The flexible tube 12 receives the collar tie 16 of the trachea tube 18 therein. The flexible tube 12 has a length about equal to a length of the collar tie 16 of the trachea tube 18. The flexible tube 12 is constructed of a soft and comfortable fabric. This construction is necessary so as not to irritate the skin of the neck while the flexible tube 12 is worn.

The flexible tube 12 is color-coordinated with a selected outfit worn by a person wearing the trachea tube 18. This feature will allow the trachea tube 18 to be essentially disguised. This is an important feature especially for children who do not want to appear different from other children. The flexible tube 12 has a generally rectangular configuration defined by essentially planar front and back walls 20,22. The flexible tube 12 includes arcuate side walls 24 coupling with the front and back walls 20,22 whereby the opposed open ends 14 are narrow and slot-like to correspond with a band-like appearance of the collar tie 16. Additionally, the flexible tube 12 could be provided with indicia thereon to further enhance the appearance of the present invention.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A decorative trach tie cover for covering the collar tie of a trachea tube to coordinate with selected items of clothing comprising, in combination:

a flexible tube having opposed open ends, the flexible tube receiving the collar tie of the trachea tube therein, the flexible tube having a length about equal to a length of the collar tie of the trachea tube, the flexible tube being constructed of a soft and comfortable fabric.

2. The decorative trach tie cover as set forth in claim 1, wherein the flexible tube is color-coordinated with a selected outfit worn by a person wearing the trachea tube.

3. The decorative trach tie cover as set forth in claim 1, wherein the flexible tube has a generally rectangular configuration defined by essentially planar front and back walls, the flexible tube including arcuate side walls coupling with the front and back walls whereby the opposed open ends are narrow and slot-like to correspond with a band-like appearance of the collar tie.

\* \* \* \* \*

UNITED STATES PATENT AND TRADEMARK OFFICE
CERTIFICATE OF CORRECTION

PATENT NO.     : 6,412,117 B1
DATED          : July 10, 2001
INVENTOR(S)    : Holmes et al.

It is certified that error appears in the above-identified patent and that said Letters Patent is hereby corrected as shown below:

<u>Title page,</u>
Item [75], Inventors, should read -- Bridgett Holmes; Erma Randle and Jayne Hallahan, 1715 Sunflower Avenue. #7, Glendora, all of CA --.

Signed and Sealed this

Twenty-sixth Day of August, 2003

JAMES E. ROGAN
*Director of the United States Patent and Trademark Office*